United States Patent
Cleary et al.

(10) Patent No.: US 9,165,253 B2
(45) Date of Patent: Oct. 20, 2015

(54) METHOD OF EVALUATING GENOMIC SEQUENCES

(71) Applicant: Real Time Genomics, Inc., San Bruno, CA (US)

(72) Inventors: John Gerald Cleary, Hamilton (NZ); Barry Mark Utting, Beerwah (AU)

(73) Assignee: Real Time Genomics Limited, Hamilton Central (NZ)

( * ) Notice: Subject to any disclaimer, the term of this patent is extended or adjusted under 35 U.S.C. 154(b) by 228 days.

(21) Appl. No.: 14/015,295

(22) Filed: Aug. 30, 2013

(65) Prior Publication Data

US 2014/0067749 A1    Mar. 6, 2014

Related U.S. Application Data

(60) Provisional application No. 61/695,408, filed on Aug. 31, 2012.

(51) Int. Cl.

| | |
|---|---|
| *G06F 9/44* | (2006.01) |
| *G06N 7/02* | (2006.01) |
| *G06N 7/06* | (2006.01) |
| *G06N 5/04* | (2006.01) |
| *G06F 19/22* | (2011.01) |
| *G06F 19/24* | (2011.01) |

(52) U.S. Cl.
CPC ............ *G06N 5/048* (2013.01); *G06F 19/22* (2013.01); *G06F 19/24* (2013.01)

(58) Field of Classification Search
USPC ........................................................ 706/52
See application file for complete search history.

(56) References Cited

U.S. PATENT DOCUMENTS

| | | | |
|---|---|---|---|
| 7,561,972 B1 * | 7/2009 | Welch et al. ................ | 702/19 |
| 7,561,973 B1 * | 7/2009 | Welch et al. ................ | 702/19 |

(Continued)

FOREIGN PATENT DOCUMENTS

| | | |
|---|---|---|
| WO | WO 2010/056131 A1 | 5/2010 |
| WO | WO 2011/145954 A1 | 11/2011 |

(Continued)

OTHER PUBLICATIONS

Remote protein homology detection using a modularity-based approach, Juan Mei; Ji Zhao; Xiaojian Yang; Weican Zhou Information Science and Technology (ICIST), 2011 International Conference on Year: 2011 pp. 1287-1291, DOI: 10.1109/ICIST.2011.5765074.*

(Continued)

*Primary Examiner* — Michael B Holmes
(74) *Attorney, Agent, or Firm* — Finnegan, Henderson, Farabow, Garrett & Dunner, LLP

(57) ABSTRACT

Methods of calling genomic sequence values in complex calling regions are disclosed. Following a preliminary sequence alignment a complex calling region may be identified where no sequence values satisfy preliminary alignment criteria. Potential hypotheses may be formulated for the complex calling region and the probability of each hypothesis representing a correct alignment may be calculated by evaluating the probability of each hypothesis being correct for the reads and the probability of each hypothesis occurring. The hypothesis best satisfying hypothesis selection criteria may be selected. The method may include an evaluation of possible indels in the complex calling region.

23 Claims, 3 Drawing Sheets

(56) References Cited

U.S. PATENT DOCUMENTS

| | | | |
|---|---|---|---|
| 7,640,256 B2 | 12/2009 | Inglis | |
| 8,126,653 B2* | 2/2012 | Welch et al. | 702/19 |
| 8,401,798 B2* | 3/2013 | Welch et al. | 702/19 |
| 2003/0033263 A1* | 2/2003 | Cleary | 706/12 |
| 2006/0184460 A1* | 8/2006 | Cleary | 706/12 |
| 2011/0264377 A1* | 10/2011 | Cleary | 702/19 |
| 2011/0301862 A1 | 12/2011 | Petrov | |
| 2013/0138355 A1 | 5/2013 | Inglis et al. | |
| 2013/0166221 A1* | 6/2013 | Inglis et al. | 702/20 |
| 2013/0309660 A1* | 11/2013 | Inglis et al. | 435/6.1 |
| 2014/0012513 A1* | 1/2014 | Cleary et al. | 702/20 |
| 2014/0057793 A1* | 2/2014 | Cleary et al. | 506/2 |
| 2014/0058681 A1* | 2/2014 | Cleary et al. | 702/19 |
| 2014/0067749 A1* | 3/2014 | Cleary et al. | 706/52 |

FOREIGN PATENT DOCUMENTS

| | | |
|---|---|---|
| WO | WO 2011/145955 A1 | 11/2011 |
| WO | WO 2012/039633 A2 | 3/2012 |

OTHER PUBLICATIONS

Structure of Thaumatin-Like Protein was Predicted and Analysis by Bioinformatics Methods, Shi, M.-w.; Wang, B.-Z.; Cheng, X.-I.; Wang, J.-H.; Yangrui, Q.-L.L. Bioinformatics and Biomedical Engineering, 2008. ICBBE 2008. The 2nd International Conference on Year: 2008 pp. 88-92, DOI: 10.1109/ICBBE.2008.28.*

A Weighted Principal Component Analysis and Its Application to Gene Expression Data, Pinto da Costa, J.F.; Alonso, H.; Roque, L. Computational Biology and Bioinformatics, IEEE/ACM Transactions on Year: 2011, vol. 8, Issue: 1 pp. 246-252, DOI: 10.1109/TCBB.2009.61.*

Feature extraction methods for mutation screening, Kaya, H.; Oguducu, S.G. Signal Processing and Communications Applications (SIU), 2011 IEEE 19th Conference on Year: 2011 pp. 698-701, DOI: 10.1109/SIU.2011.5929746.*

Beaumont et al., "The Bayesian revolution in genetics," *Nat Rev Genet*, 5: 251-261 (2004).

Depristo et al., "A framework for variation discovery and genotyping using next-generation DNA sequencing data," *Nature Genetics*, 43: 491-498 (2011).

Koller et al., *Probabilistic Graphical Models—Principles and Techniques*, Chapters 3 and 9, MIT Press, Cambridge, MA (2009).

Li et al., "Mapping short DNA sequencing reads and calling variants using mapping quality scores," *Genome Res.*, 18: 1851-1858 (2008).

Li et al., "SNP detection for massively parallel whole-genome resequencing," *Genome Res.*, 19: 1124-1132 (2009).

Peng et al., "Rare variant detection using family-based sequencing analysis," *PNAS*, 110(10): 3985-3990 (2013).

Shao et al., "A population model for genotyping indels from next-generation sequence data," *Nucleic Acids Research*, 41(3) e46, 6 pages (2013).

Sincan et al., "VAR-MD: A Tool to Analyze Whole Exome—Genome Variants in Small Human Pedigrees with Mendelian Inheritance," *Human Mutation*, 33(4), Article first published online: Feb. 24, 2012.

Teer et al., "Systematic comparison of three genomic enrichment methods for massively parallel DNA sequencing," *Genome Res.*, 20: 1420-1431 (2010), with Supplemental Methods: MPG (2 pages).

Pending U.S. Appl. No. 13/848,653, filed Mar. 21, 2013.
Pending U.S. Appl. No. 13/971,630, filed Aug. 20, 2013.
Pending U.S. Appl. No. 13/971,654, filed Aug. 20, 2013.
Pending U.S. Appl. No. 13/925,704, filed Jun. 24, 2013.

* cited by examiner

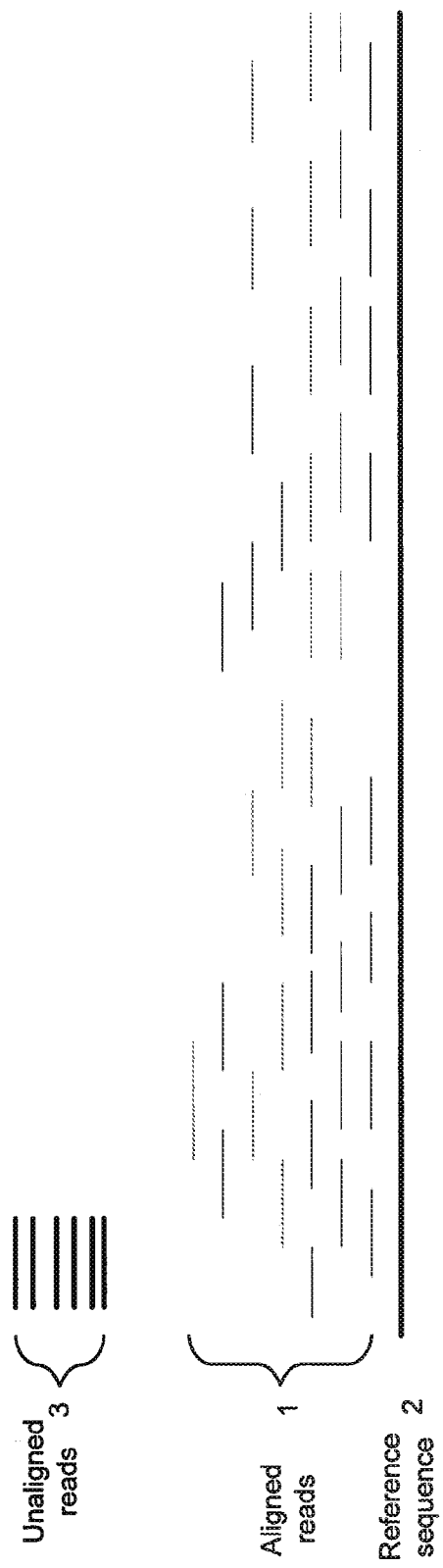
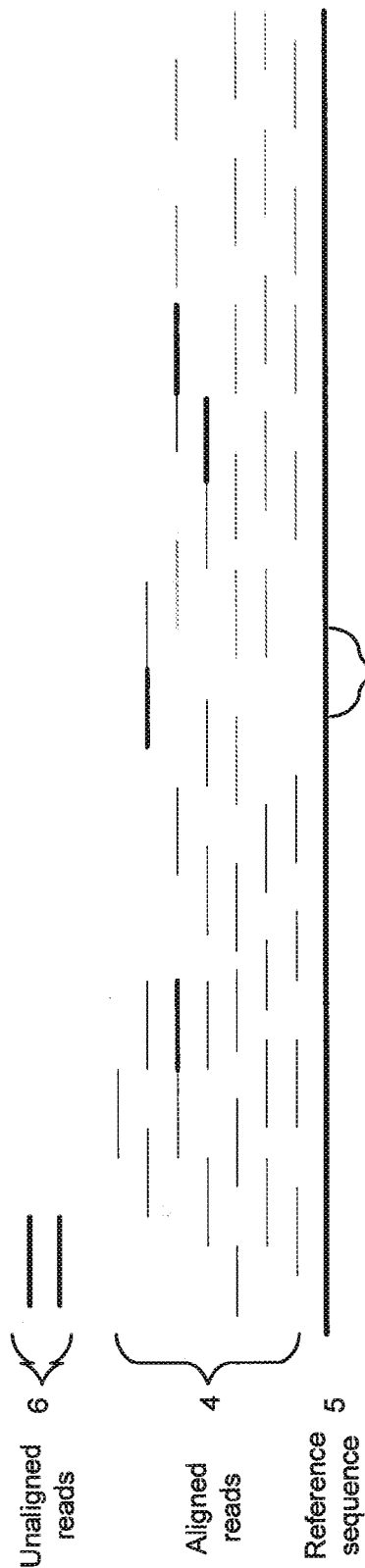

METHOD OF EVALUATING GENOMIC SEQUENCES

CROSS-REFERENCE TO RELATED APPLICATIONS

This application claims priority to U.S. Provisional Application No. 61/695,408, filed Aug. 31, 2012, which is incorporated by reference herein.

The inventions described herein relate to a method for evaluating genomic sequences and systems therefor.

There have been great advances in genomic sequencing in recent times. Sequencing machines can generate reads ever more rapidly with increasingly accurate results. However, there remain errors in the reads produced and during the process of read alignment the reads must be assembled as best as possible to generate the most accurate genomic sequence for the sample possible. The process of "calling" a value of the sequence from the reads requires consideration of a range of relevant factors and potential sources of errors.

A wide range of algorithms for calling sequence values have been employed. Some use filtering techniques but this potentially loses information that may assist in making a call or values that upon more thorough investigation may be the best calls. Others, such as Gotoh and Markov evaluate of a wide range of possible solutions but not in a principled model that properly weights all factors. The calling confidence with such approaches is less than desired.

It is an object of the invention to provide an improved method of evaluating genomic sequences that overcomes at least some of these problems or to at least provide the public with a useful choice.

In an embodiment, the invention provides a method of calling genomic sequence values in complex calling regions based on a plurality of read values, the method performed by one or more processors executing program instructions stored on one or more memories, the instructions causing the one or more processors to perform the method comprising:
 a. performing a preliminary sequence alignment based on the reads being positioned with respect to a reference genome at a required confidence level, wherein at least some reads that cannot initially be aligned are combined to form one or more assembly of reads that are utilised during the preliminary alignment;
 b. identifying a complex calling region where no values satisfy preliminary alignment criteria;
 c. formulating a plurality of hypotheses as to the sequence values in the complex calling region;
 d. calculating the probability of each hypothesis representing a correct alignment by evaluating the probability of each hypothesis being correct for the reads and the probability of each hypothesis occurring; and
 e. selecting the hypothesis best satisfying hypothesis selection criteria.

In another embodiment, the invention provides A method of calling genomic sequence values in complex calling regions based on a plurality of read values, the method performed by one or more processors executing program instructions stored on one or more memories, the instructions causing the one or more processors to perform the method comprising:
 a. performing a preliminary sequence alignment based on the reads;
 b. identifying a complex calling region where no values satisfy preliminary alignment criteria, wherein a region is considered a complex calling region where the confidence in calling the region is below a first threshold, a region is considered a region of interest where the confidence in calling the region is below a second threshold, the second threshold being higher than the first threshold, and where a region of interest occurs within a defined number of values of a complex calling region the complex calling region is expanded to encompass the region of interest and intermediate values up to and including the complex calling region;
 c. formulating a plurality of hypotheses as to the sequence values in the complex calling region;
 d. calculating the probability of each hypothesis representing a correct alignment by evaluating the probability of each hypothesis being correct for the reads and the probability of each hypothesis occurring; and
 e. selecting the hypothesis best satisfying hypothesis selection criteria.

In another embodiment, the invention provides a method of calling genomic sequence values in complex calling regions based on a plurality of read values, the method performed by one or more processors executing program instructions stored on one or more memories, the instructions causing the one or more processors to perform the method comprising:
 a. performing a preliminary sequence alignment based on the reads;
 b. identifying a complex calling region where no values satisfy preliminary alignment criteria;
 c. formulating a plurality of hypotheses as to the sequence values in the complex calling region;
 d. calculating the probability of each hypothesis representing a correct alignment by evaluating the probability of each hypothesis being correct for the reads and the probability of each hypothesis occurring; and
 e. selecting the hypothesis best satisfying hypothesis selection criteria,
 wherein each hypothesis is evaluated with respect to each read considering at each sequence position the possibility of an indel.

In another embodiment, the invention provides a system for calling genomic sequence values in complex calling regions based on a plurality of read values, the system comprising:
 one or more processors configured to execute one or more modules;
 and a memory storing the one or more modules, the modules comprising:
 a. code for performing a preliminary sequence alignment based on the reads being positioned with respect to a reference genome at a required confidence level, wherein at least some reads that cannot initially be aligned are combined to form one or more assembly of reads that are utilised during the preliminary alignment;
 b. code for identifying a complex calling region where no values satisfy preliminary alignment criteria;
 c. code for formulating a plurality of hypotheses as to the sequence values in the complex calling region;
 d. code for calculating the probability of each hypothesis representing a correct alignment by evaluating the probability of each hypothesis being correct for the reads and the probability of each hypothesis occurring; and
 e. code for selecting the hypothesis best satisfying hypothesis selection criteria.

In another embodiment, the invention provides a method of calling genomic sequence values for a region based on a plurality of read values, the method performed by one or more processors executing program instructions stored on one or more memories, the instructions causing the one or more processors to perform the method comprising:

a. formulating a plurality of hypotheses as to the sequence values in the region;
b. calculating the probability of each hypothesis representing a correct alignment by evaluating the probability of each hypothesis occurring and the probability of each hypothesis being correct for the reads considering at each sequence position the possibility of modification of a sequence value; and
c. selecting the hypothesis best satisfying hypothesis selection criteria,
wherein each hypothesis is evaluated with respect to each read considering at each sequence position the possibility of an indel.

Additional objects and advantages of the invention will be set forth in part in the description which follows.

It is acknowledged that the terms "comprise," "comprises" and "comprising" may, under varying jurisdictions, be attributed with either an exclusive or an inclusive meaning. For the purpose of this specification, and unless otherwise noted, these terms are intended to have an inclusive meaning—i.e. they will be taken to mean an inclusion of the listed components which the use directly references, and possibly also of other non-specified components or elements.

Reference to any prior art in this specification does not constitute an admission that such prior art forms part of the common general knowledge.

It is to be understood that both the foregoing general description and the following detailed description are exemplary and explanatory only and are not restrictive of the invention, as claimed.

BRIEF DESCRIPTION OF THE DRAWINGS

The accompanying drawings which are incorporated in and constitute part of the specification, illustrate embodiments of the invention and, together with the general description of the invention given above, and the detailed description of exemplary embodiments given below, serve to explain the principles of the invention. Reference will now be made to the accompanying drawings showing exemplary embodiments of this disclosure. In the drawings:

FIG. 1 shows diagrammatically a preliminary read alignment.

FIG. 2 shows diagrammatically a preliminary read alignment after unaligned read assembly.

DETAILED DESCRIPTION

Figure 3:
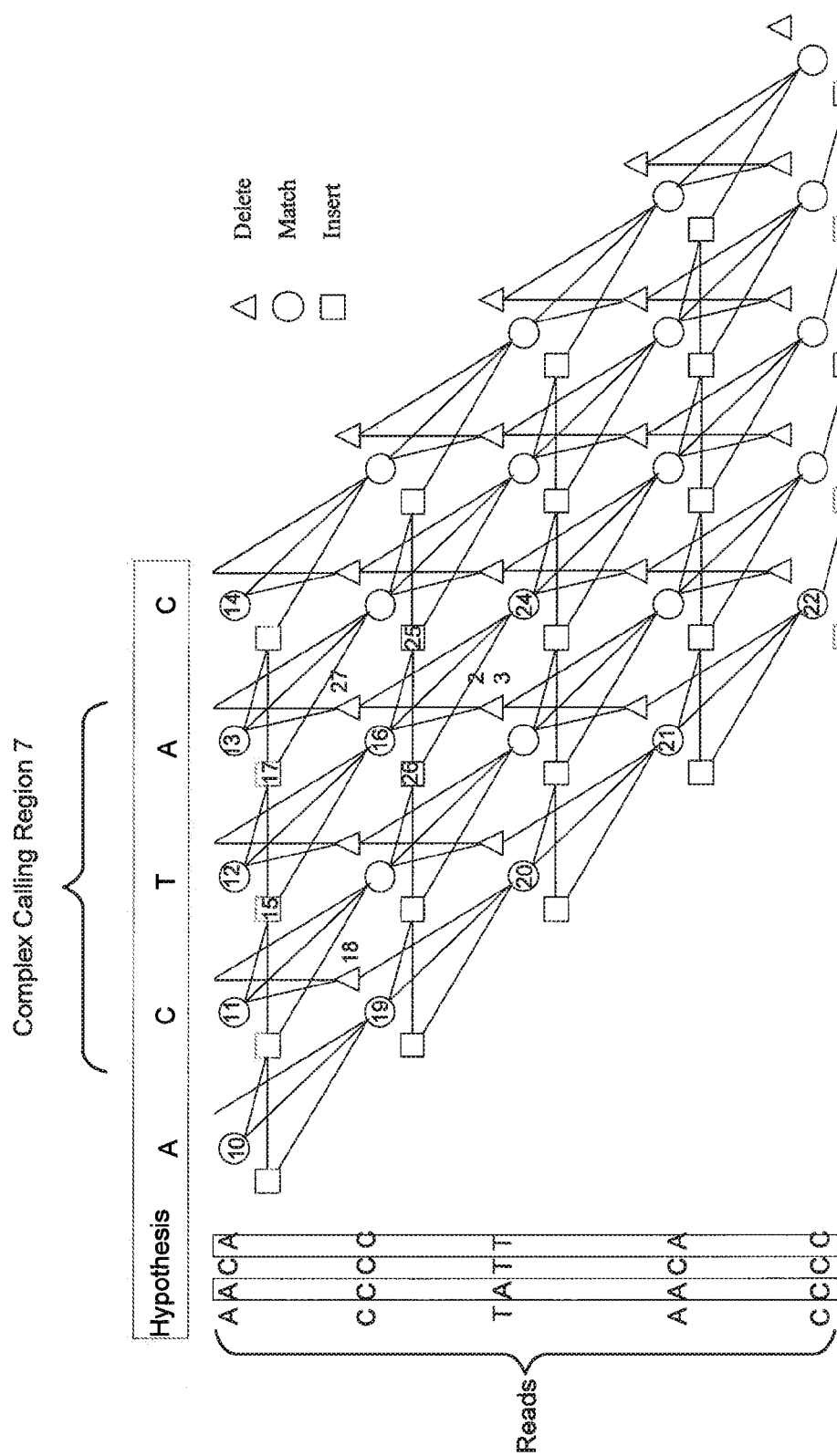
FIG. 3 shows a methodology for determining the probability associated with a hypothesis.

When developing a representation of a genomic sequence for an organism, sequencing machines produce many reads of short portions of the subject genomic sequence (typically DNA, RNA or proteins). These reads (genomic sequence information) must be aligned and then "calls" must be made as to values of the sequence at each location (e.g. individual bases for DNA). There may typically be only a few reads (and sometimes none) at a particular location or very many reads in others.

Known techniques may be employed to perform preliminary alignment, including those described in International Patent Application Nos. PCT/NZ2005/000134 and PCT/NZ2009/000245. Such alignment aims to align the multitude of reads produced by a sequencing machine with a reference sequence (e.g., published SNPs for the genome being evaluated). As illustrated in FIG. 1 a first alignment may result in a number of reads having an acceptable alignment with the reference sequence and a number of unaligned reads.

The unaligned reads may be further processed to see if some alignment can be achieved. This may include assembling two or more reads to form an assembled read that may be aligned in like manner to a standard read. One read may have some association with another read enabling them to be combined to form an assembled read. Paired end reads may have such an association. In the case of paired end reads it is known that the reads occur within a certain proximity of each other and this may be used to associate and position an unaligned read. Alternatively an unaligned read may have an association with an external reference sequence that enables it to be combined with the external reference sequence to assist in its positioning. FIG. 2 illustrates alignment after such assembled reads (thick lines) have been incorporated.

Error is inherent in the sequencing process. In some cases all reads are consistent or "simple calls" may be made using conventional calling techniques. There are typically "complex calling regions" that may span a single or several values where more sophisticated analysis is required to make a reliable call. A region may be identified as a complex calling region where the confidence in calling the region may be below a first threshold using simple calling techniques or there may be characteristics of the region indicating that deeper analysis is desirable. These characteristics may be numbers of insertions and or deletions, the value and proximity of calls (e.g. a number of low confidence calls close to each other) etc. In some embodiments, a region is identified as a complex calling region based on information from previous calling of samples, or aggregated information from a population of samples. The information from previous calling of samples or aggregated information from a population of samples can comprise, e.g., whether the region had been identified as a complex calling region, whether indels had been called, or whether calls were made below a threshold confidence level in a number (one, two, three, etc.) or all of the previous samples, or in a proportion of the previous samples, e.g., 5%, 10%, 20%, 25%, 33%, 50%, 67%, 75%, 80%, 90%, or 95%. In some embodiments, externally supplied high and/or low confidence regions may be supplied which alter the thresholds for when a region is identified as a complex calling region. Thus, in such embodiments, the first threshold discussed above has different values in regions of the genome identified in the externally supplied high and/or low confidence regions. In some embodiments, one or more of the following are supplied as low confidence regions: regions with known segmental duplications absent from the GRCh37 reference assembly, available from the humanparalogy.gs.washington.edu HTTP server; regions identified by RepeatMasker software as "simple repeats" (including tandem repeats) (see Tarailo-Graovac et al., "Using RepeatMasker to Identify Repetitive Elements in Genomic Sequences," Curr. Protocols in Bioinformatics, 25:4.10.1-4.10.14 (2009), which is incorporated by reference herein); and regions excluded from the NA12878 confident dataset (see Zook et al., "Integrating sequencing datasets to form highly confident SNP and indel genotype calls for a whole human genome," available as file 1307.4661.pdf in path ftp/arxiv/papers/1307/ on HTTP server arxiv.org, which is incorporated by reference herein). There may also be regions of interest where the confidence in calling the region is below a second threshold, higher than the first threshold. Where a region of interest occurs within a defined number of values (e.g. 5 bases) of a complex calling region the complex calling region may be expanded to encompass the region of interest and intermediate values up to and including the complex calling region may be considered a complex calling region. In this way complex calling regions may propagate out where neighboring values have a low confidence, although not low enough to themselves trigger identification as a complex calling region. This enables the confidence in neighboring calls to influence the classification of local calls.

Referring now to FIG. 3 the methodology for evaluating the probability associated with possible solutions (hypotheses) in a complex calling region will be illustrated. This is a highly simplified example given simply to illustrate the methodology. In the example illustrated in FIG. 1 the first hypothesis is that the base values in a DNA sequence are ACTAC. In the diagram the circles indicate that the values match, which in this case means that the first value in the 5 base sequence remains as A. Thus the evaluation at node 10 is the probability that the base A occurs at this position. Likewise at nodes 11 to 14 the nodes evaluate the probability that the value is C,T,A,C respectively. Thus node 10 considers the probability that the A of the hypothesis is correct given read values A,A,C,A. Likewise node 19 considers the probability that the C of the hypothesis is correct given read values C,C,C,C.

A square, such as square 15, represents an insertion. Thus node 15 evaluates the probability of an insertion occurring. From node 15 processing may advance either to node 16 or node 17. Node 16 evaluates the probability that following the insertion the next value is an A (i.e. the probability of the third bases of the reads (T,A,T,T) occurring for the 4$^{th}$ base of the hypothesis (A)). Node 17 evaluates the probability that there is another insertion.

A triangle such as node 18 represents a deletion. This node evaluates the probability that a base has been deleted between C and T. Processing then passes to node 20 which evaluates the probability that following the deletion the base value T corresponds to the third value of the reads (i.e. the probability of the third bases of the reads (T,A,T,T) occurring for the 3rd base of the hypothesis (T)).

The probability calculated at each node is propagated down through all nodes. Thus nodes 10 to 14 calculate the probability that the base of the hypothesis is correct given the reads for the complex calling region 7.

Where the circle nodes are followed through diagonally (i.e. nodes 10, 19, 20, 21, 22) consideration is given to the probability that the unaltered hypothesis is correct when evaluated against all the reads in the complex calling region. Node 10 will evaluate the probability associated with A in relation to the values of the reads in the complex calling region (i.e. in this simplified example A,A,C,A from the reads ACTAC, ACAAC, CCTCC and ACTAC). Node 19 will evaluate the probability associated with C in relation to the values of the reads in the complex calling region (i.e. in this example A,C,C,C from the reads ACTAC, ACAAC, CCTCC and ACTAC).

The probability calculated at each node is propagated down. Thus, for example, the probability at node 16 is multiplied by probabilities of a deletion, match and insertion in its preceding nodes to produce the probability it supplies to subsequent nodes 23, 24 and 25 respectively. For a downstream node, such as node 24 its input probability will be the sum of the probabilities supplied by nodes 16, 26 and 27. The sum of all probabilities output by the bottom most nodes form the probability for the hypothesis. In this manner all possible scenarios of insertions, deletions and identity may be considered and given their appropriate weighting.

Applying a Bayesian model to evaluate each node, the probability of a hypothesis (proposed sequence values for the complex calling region) being correct given the data (reads) is the normalised value of the probability of the hypothesis occurring (Prior) times the probability of the data occurring given the hypothesis (Model). Thus, in some embodiments, the probability of a hypothesis being correct given the data is expressed as:

$$P(H|D) = \frac{P(H) \times P(D|H)}{\sum P(H) \times P(D|H)}$$

where:
P(H|D) is the probability of a hypothesis H being correct for all reads D,
P(H) is the probability of the hypothesis occurring, independent of the reads D,
P(D|H) the probability of the reads D occurring given the hypothesis;
  P(D|H)=ΠP(d|H) is computed as the product of the probabilities of the all the reads d contained in D. It is the expression P(d|H) which is computed in process described above.
Σ(H)×P(D|H) is the sum of all probabilities for all hypotheses—which is used to normalise the results.

Evaluation of a hypothesis with respect to reads can be performed by modifying a reference sequence to match the hypothesis. For example, if the reference sequence is GATTAGATTA and the hypothesis is that the actual base at position 6 is C, a modified reference sequence GATTA-CATTA would be used. Thus, the reads would be matched across the hypothesis and the adjacent parts of the reference.

The probability of an hypothesis occurring P(H) may be based on historical sequence information, i.e. comparing the sequence in the complex calling region with published sequence information (such as the 1000 Genomes Project or dbSNP) in the area of interest, that is, the probability of that sequence occurring, irrespective of the read data.

In some embodiments, for example when calling variants in autosomes in eukaryotic organisms, it is wished to compute the probability of a diploid hypothesis. Consider such a diploid hypothesis H which consists of two haploid hypotheses $H_1$ and $H_2$. Then P(d|H) can be computed using the formula $$P(d|H) = \frac{P(d|H_1) + P(d|H_2)}{2}$$

The final expression P(H|D) can be computed using this formula and the other formulae above.

In some embodiments, the probability of an hypothesis P(H) is calculated using information from calling in other samples or from aggregated samples. Alternatively, it can be calculated by computing the similarity of the hypothesis to the reference by inserting the actual reference R as the hypothesis and treating the hypothesis H as a read, then using the probability as the prior P(H). That is, P(H)=P(H|R). This probability P(H|R) in which R is treated as a hypothesis and H is treated as a read can be calculated as described above with respect to calculation of P(H|D).

The possible hypotheses may include:
(1) All possible sequences for the complex calling region. This is the most processing intensive approach and may be most appropriate where deep investigation of a region is required or the sequence length is short.
(2) All read values occurring in the complex calling region. It is unlikely that a sequence value not occurring in any read will be the correct value and so this approach limits computation without significant reduction in calling confidence.
(3) Read values above may be combined with "assemblies of reads" as described above. Such "assemblies of reads" may combine "associated reads". This association may be paired end reads or reads that are associated with external reference sequences (i.e. "pseudo reads" from publications or external events; not from "wet" reads from a sequencer). Such assembled reads may be combined across multiple samples.

The hypotheses may be pruned where appropriate. This will depend upon the nature of the calling (i.e. for refined calling of a small complex calling region there may be no pruning whereas for simple sequence evaluation with a large complex calling region there may be significant pruning).

Options for pruning hypotheses include:
(1) Prune hypotheses to exclude those having a probability of occurrence below a threshold level (e.g. use probabilities from preliminary calling).
(2) Where hypotheses are based on reads exclude hypotheses that occur in the reads at a frequency below a threshold level.
(3) Exclude hypotheses having a low frequency of occurrence in similar populations from historic SNP data.
(4) Exclude hypotheses having a probability below a threshold level based on contextual information—e.g. a hypothesis would have a very low probability based on Mendelian inheritance where genomic information for family members is known.

Model values (i.e. P(D|H)) represent the probability of the genomic reads (D) occurring given the hypothesis (H). These Model values may be calculated on the basis of one or more of:
(1) quality scores for sequencing machines (i.e. the figures as to sequencing accuracy published by sequencing machine manufacturers);
(2) calibrated quality scores (i.e. quality figures determined from preliminary alignment);
(3) mapping scores (such as MAPQ scores); and/or
(4) the chemistry of the sequences (there may be different probabilities of error, insertion, deletion etc depending upon the particular base sequence values—such as for homopolymer sequences).

When considering the probability of indels the following approaches may be employed:
(a) the probability of an insertion may be based on tables giving the probability of the insertion based on a single previous or subsequent sequence position.
(b) the probability of an insertion may be based on tables giving the probability of the insertion based on multiple previous or subsequent sequence positions.
(c) the probability of a deletion may be based on tables giving the probability of the deletion based on a single previous or subsequent sequence position.
(d) the probability of a deletion may be based on tables giving the probability of the deletion based on multiple previous or subsequent sequence positions.

Probabilities may also be affected by other contextual information. For example knowledge of haplotype phasing from parents may be taken into account when assessing the probability of a particular base sequence. This information may also be used to fill in detail for progeny based on parental information where information is missing or unclear.

Hypotheses may also be evaluated in a prescribed order. This may be based on a weighting of hypotheses. The weighting of hypotheses may be a graduated scale or on a simple inclusion and exclusion basis. The weighting may be based upon the frequency of occurrence of a hypothesis in the sequence values and the hypotheses may be evaluated from the hypotheses having the highest weighting to those having the lowest weighting. Sex based inheritance may also be taken into account. Evaluation may be terminated before all hypotheses are evaluated if an acceptance criterion is met. The acceptance criteria may be that a hypothesis is found to have a probability above a threshold value or be based on a trend in probabilities from evaluation (e.g. continually decreasing probabilities of hypotheses).

Hypotheses may be processed in an order considered most likely to produce a call meeting a required confidence level. Hypotheses may be rated according to factors such as their frequency of occurrence in the reads, a rating score (such as a MAPQ value) etc. Processing may be terminated if a hypothesis probability is above a threshold value or is trending in a desired manner. This is a technique to speed up processing and may not be appropriate where a more detailed evaluation is required.

The probability calculated at each node may be cached so that it may be re-used if required in subsequent processing for the same values.

Figure 4:
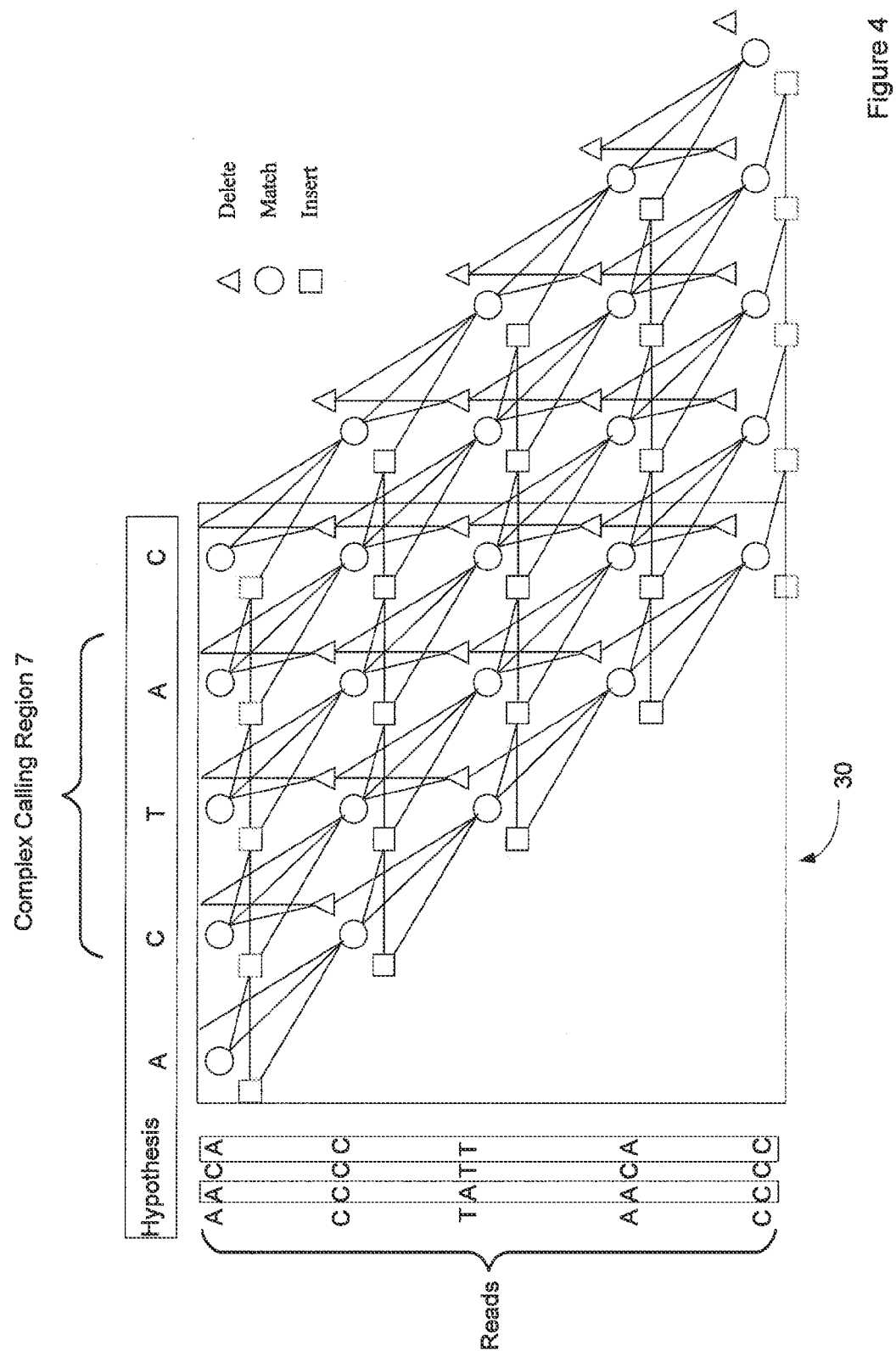
FIG. 4 shows a method of reducing computation in the method illustrated in FIG. 3.

Further, as illustrated in FIG. 4, in some embodiments, probabilities are calculated only for nodes in the region 30 as the values outside of this region have been called to a required confidence level. According to this technique probabilities may be calculated forward from the left hand side and backwards from the right hand side. As the values on either side of region 30 remain constant only the values within region 30 need be calculated forwards and backwards from each side.

It will be appreciated that the method may be used to evaluate a wide variety of sequences including DNA, RNA and proteins. According to one embodiment the method may be applied to one type of sequence and then cross checked on a translation of the sequence to another type of sequence. For example initial analysis may be performed on a DNA or RNA sequence. The sequence may then be translated into a protein sequence and checked to validate that the protein sequence is probable (e.g. cross check in protein space using Blossom matrix).

Example

The following example illustrates calculation of the probability of the hypothesis ACTAC being correct for the read ACAAC.

Given co-ordinates:
r—position on read
t—position of template
The formulae for calculating this probability are:
Match probability (the circles in the diagram)

$$M_{r,t} = (I_{r-1,t-1} + D_{r-1,t-1} + M_{r-1,t-1}) \times Ma \times \begin{cases} 1 - Q_r & R_r = T_t \\ Q_r/3 & R_r \neq T_t \end{cases}$$

Insertion probability (the squares in the diagram)

$$I_{r,t} = I_{r,t-1} \times Ex + M_{r,t-1} \times Op$$

Deletion probability (the triangles in the diagram)

$$D_{r,t} = D_{r,t-1} \times Ex + M_{r,t-1} \times Op$$

where:
Ma—the probability of a match
Op—the probability that a new gap (insertion or deletion) will be opened
Ex—the probability that a gap (insertion or deletion) will be extended
$R_r$—the nucleotide at position r on the read
$T_t$—the nucleotide at position t on the template
$Q_r$—the probability that the nucleotide at position r on the read is in error The following spreadsheet illustrates a worked example. The "delete", "Eq/SNP" and "Insert" rows correspond to the triangles, circles and squares in FIG. 3.

|    | A    | B    | C      | D       | E       | F       | G       | H       | I       | J       |
|----|------|------|--------|---------|---------|---------|---------|---------|---------|---------|
| 1  |      |      |        |         |         | GapOpen | GapExtend |       |         |         |
| 2  |      |      |        |         | Insert: | 0.00058 | 0.20000 |         |         |         |
| 3  |      |      |        |         | Delete: | 0.00083 | 0.18000 |         |         |         |
| 4  |      |      |        |         | Match:  | 0.98939 | =1 - SNP probability below | | | |
| 5  |      |      |        |         | Mismatch: | 0.00920 |       |         |         |         |
| 6  |      |      |        |         |         |         |         |         |         |         |
| 7  |      |      |        |         | Template: | A     | C       | T       | A       | C       |
| 8  |      |      |        | Delete: |         | 0.00083 | 0.00083 | 0.00083 | 0.00083 | 0.00083 |
| 9  |      |      |        | Eq/SNP: | 0.20000 | 0.20000 | 0.20000 | 0.20000 | 0.20000 |         |
| 10 | Read | Qual |        | Insert: |         |         |         |         |         |         |
| 11 |      |      |        | Delete: |         | 0.00032 | 0.00032 | 0.00032 | 0.00032 | 0.00015 |
| 12 | A    | 10   | 0.1000 | Eq/SNP: | 0.00000 | 0.17809 | 0.00662 | 0.00662 | 0.17883 | 0.00662 |
| 13 |      |      |        | Insert: | 0.00058 | 0.00012 | 0.00013 | 0.00003 | 0.00001 | 0.00011 |
| 14 |      |      |        | Delete: |         |         | 0.00006 | 0.00006 | 0.00021 | 0.00003 |
| 15 | C    | 15   | 0.0316 | Eq/SNP: | 0.00000 |         | 0.17104 | 0.00007 | 0.00007 | 0.17165 |
| 16 |      |      |        | Insert: | 0.00000 |         | 0.00000 | 0.00010 | 0.00002 | 0.00000 |
| 17 |      |      |        | Delete: |         |         |         | 0.00032 | 0.00032 | 0.00032 |
| 18 | A    | 20   | 0.0100 | Eq/SNP: | 0.00000 |         |         | 0.00056 | 0.00023 | 0.00000 |
| 19 |      |      |        | Insert: | 0.00000 |         |         | 0.00000 | 0.00000 | 0.00000 |
| 20 |      |      |        | Delete: |         |         |         |         | 0.00032 | 0.00032 |
| 21 | A    | 20   | 0.0100 | Eq/SNP: | 0.00000 |         |         |         | 0.00086 | 0.00000 |
| 22 |      |      |        | Insert: | 0.00000 |         |         |         | 0.00000 | 0.00000 |
| 23 |      |      |        | Delete: |         |         |         |         |         | 0.00032 |
| 24 | C    | 20   | 0.0100 | Eq/SNP: | 0.00000 |         |         |         |         | 0.00115 |
| 25 |      |      |        | Insert: | 0.00000 |         |         |         |         | 0.00000 |
| 26 |      |      |        | Delete: |         |         |         |         |         |         |
| 27 |      |      |        |         |         | 0.17852 | 0.17110 | 0.00088 | 0.00118 | 0.00147 |
| 28 |      |      |        | Final:  | 0.35315 |         |         |         |         |         |

The formulae for the first six columns (A-F) in the spreadsheet above are set out below (the values for OpenDelete, ExtendDelete, OpenInsert, and ExtendInsert, correspond to cells F3, G3, F2, and G2, respectively):

|      |      |                   |         |            | GapOpen |
|------|------|-------------------|---------|------------|---------|
|      |      |                   | Insert: |            | 0.00058 |
|      |      |                   | Delete: |            | 0.00083 |
|      |      |                   | Match:  |            | =1-F5-F3-F2 |
|      |      |                   | Mismatch: |          | 0.0092 |
|      |      |                   | Template: |          | A |
|      |      |                   | Delete: |            | =OpenDelete |
|      |      |                   | Eq/SNP: | =1/5       | =1/5 |
| Read | Qual |                   | Insert: |            | |
|      |      |                   | Delete: |            | =F8 * ExtendDelete + F9 * OpenDelete |
| A    | 10   | =POWER(10, -B12/10) | Eq/SNP: | 0        | =SUM(E8:E10) * IF(F$7 = $A12, Match * (1 – $C12), $C12/3 * Match) |
|      |      |                   | Insert: | =OpenInsert | =E12 * OpenInsert + E13 * ExtendInsert |
|      |      |                   | Delete: |            | |
| C    | 15   | =POWER(10, -B15/10) | Eq/SNP: | 0        | |
|      |      |                   | Insert: | 0          | |
|      |      |                   | Delete: |            | |
| A    | 20   | =POWER(10, -B18/10) | Eq/SNP: | 0        | |
|      |      |                   | Insert: | 0          | |
|      |      |                   | Delete: |            | |
| A    | 20   | =POWER(10, -B21/10) | Eq/SNP: | 0        | |
|      |      |                   | Insert: | 0          | |
|      |      |                   | Delete: |            | |
| C    | 20   | =POWER(10, -B24/10) | Eq/SNP: | 0        | |
|      |      |                   | Insert: | 0          | |
|      |      |                   | Delete: |            | |
|      |      |                   |         |            | =SUM(F11:F26) |
|      |      |                   | Final:  | =SUM(F27:J27) | |

The formulae for the 7$^{th}$ and 8$^{th}$ columns (G-H) are set out below:

| GapExtend |   |
|-----------|---|
| 0.2       |   |
| 0.18      |   |
| = 1—SNP probability below | |
| C         | T |
| =OpenDelete | =OpenDelete |
| =1/5      | =1/5 |
| =G8 * ExtendDelete + G9 * OpenDelete | =H8 * ExtendDelete + H9 * OpenDelete |

-continued

| | |
|---|---|
| =SUM(F8:F10) * IF (G$7 = $A12, Match * (1 − $C12), $C12/3 * Match) | =SUM(G8:G10) * IF(H$7 = $A12, Match * (1 − $C12), $C12/3 * Match) |
| =F12 * OpenInsert + F13 * ExtendInsert | =G12 * OpenInsert + G13 * ExtendInsert |
| =G11 * ExtendDelete + G12 * OpenDelete | =H11 * ExtendDelete + H12 * OpenDelete |
| =SUM(F11:F13) * IF(G$7 = $A15, Match * (1 − $C15), $C15/3 * Match) | =SUM(G11:G13) * IF(H$7 = $A15, Match * (1 − $C15), $C15/3 * Match) |
| =F15 * OpenInsert + F16 * ExtendInsert | =G15 * OpenInsert + G16 * ExtendInsert |
| | 0.0003154 |
| | =SUM(G14:G16) * IF(H$7 = $A18, Match * (1 − $C18), $C18/3 * Match) |
| | =G18 * OpenInsert + G19 * ExtendInsert |
| =SUM(G14:G26) | =SUM(H17:H26) |

The formulae for the 9$^{th}$ and 10$^{th}$ columns (I-J) are set out below:

| A | C |
|---|---|
| =OpenDelete | =OpenDelete |
| =1/5 | |
| =I8 * ExtendDelete + I9 * OpenDelete | =J8 * ExtendDelete + J9 * OpenDelete |
| =SUM(H8:H10) * IF(I$7 = $A12, Match * (1 − $C12), $C12/3 * Match) | =SUM(I8:I10) * IF(J$7 = $A12, Match * (1 − $C12), $C12/3 * Match) |
| =H12 * OpenInsert + H13 * ExtendInsert | =I12 * OpenInsert + I13 * ExtendInsert |
| =I11 * ExtendDelete + I12 * OpenDelete | =J11 * ExtendDelete + J12 * OpenDelete |
| =SUM(H11:H13) * IF(I$7 = $A15, Match * (1 − $C15), $C15/3 * Match) | =SUM(I11:I13) * IF(J$7 = $A15, Match * (1 − $C15), $C15/3 * Match) |
| =H15 * OpenInsert + H16 * ExtendInsert | =I15 * OpenInsert + I16 * ExtendInsert |
| 0.0003154 | 0.0003154 |
| =SUM(H14:H16) * IF(I$7 = $A18, Match * (1 − $C18), $C18/3 * Match) | =SUM(I14:I16) * IF(J$7 = $A18, Match * (1 − $C18), $C18/3 * Match) |
| =H18 * OpenInsert + H19 * ExtendInsert | =I18 * OpenInsert + I19 * ExtendInsert |
| 0.0003154 | |
| =SUM(H17:H19) * IF(I$7 = $A21, Match * (1 − $C21), $C21/3 * Match) | =SUM(I17:I19) * IF(J$7 = $A21, Match * (1 − $C21), $C21/3 * Match) |
| =H21 * OpenInsert + H22 * ExtendInsert | =I21 * OpenInsert + I22 * ExtendInsert |
| | 0.0003154 |
| | =SUM(I20:I22) * 1F(J$7 = $A24, Match * (1 − $C24), $C24/3 * Match) |
| | =I24 * OpenInsert + I25 * ExtendInsert |
| =SUM(I20:I26) | =SUM(J23:J26) |

In some embodiments, this method is implemented using SIMD (single instruction, multiple data) instructions allowing parallel processing inside a CPU. Their accessibility in software using intrinsic functions allows the software designer to use localized parallelism, which can provide a large speed improvement.

SIMD instructions could be added to generalized CPUs (such as the Intel range of processors) or a custom programmable CPU that could execute parts of the above method in parallel. Such SIMD instructions would allow the evaluation of the function (DNA, RNA or Protein), by loading the regions of DNA or protein strings into a CPU, executing the hardware instructions to compute the calculation, and returning the result, as is illustrated in FIG. 3.

The following are two embodiments of this form of instruction. In a "global" version, the DNA would be loaded into the CPU and a single SIMD instruction would be called to determine the answer. The second embodiment would be to break down the computation into chunks of "local" parallelism, potentially calculating one or more constrained regions such as shown in FIG. 4. This approach may significantly increase the speed of variant calling.

There are thus provided methods allowing high quality calls to be made with consistent scoring. The models provide a principled way of combining multiple effects with the ability to dynamically update model values as information is obtained. The models provide fast resolution of complex calling problems with improved accuracy.

As would be well understood by those of skill in the art, the disclosed methods may be performed by one or more processors executing program instructions stored on one or more memories. Certain embodiments comprise systems for calling genomic sequence values in complex calling regions based on a plurality of read values, wherein the modules comprise such exemplary hardware components.

LISTING OF EMBODIMENTS

The following is a listing of exemplary embodiments:
1. A method of calling genomic sequence values in complex calling regions based on a plurality of read values, the method performed by one or more processors executing program instructions stored on one or more memories, the instructions causing the one or more processors to perform the method comprising:
    a. performing a preliminary sequence alignment based on the reads;
    b. identifying a complex calling region where no values satisfy preliminary alignment criteria;
    c. formulating a plurality of hypotheses as to the sequence values in the complex calling region;
    d. calculating the probability of each hypothesis representing a correct alignment by evaluating the probability of each hypothesis being correct for the reads and the probability of each hypothesis occurring; and e. selecting the hypothesis best satisfying hypothesis selection criteria.

2. A method of calling genomic sequence values in complex calling regions based on a plurality of read values, the method performed by one or more processors executing program instructions stored on one or more memories, the instructions causing the one or more processors to perform the method comprising:
   d. performing a preliminary sequence alignment based on the reads;
   e. identifying a complex calling region where no values satisfy preliminary alignment criteria, wherein a region is considered a complex calling region where the confidence in calling the region is below a first threshold, a region is considered a region of interest where the confidence in calling the region is below a second threshold, the second threshold being higher than the first threshold, and where a region of interest occurs within a defined number of values of a complex calling region the complex calling region is expanded to encompass the region of interest and intermediate values up to and including the complex calling region;
   f. formulating a plurality of hypotheses as to the sequence values in the complex calling region;
   g. calculating the probability of each hypothesis representing a correct alignment by evaluating the probability of each hypothesis being correct for the reads and the probability of each hypothesis occurring; and
   h. selecting the hypothesis best satisfying hypothesis selection criteria.

3. The method according to any one of the preceding embodiments wherein the probability of a hypothesis being correct for the reads is calculated according to:

$$P(H|D) = \frac{P(H) \times P(D|H)}{\sum P(H) \times P(D|H)}$$

where:
P(H|D) is the probability of a hypothesis H being correct for all reads D,
P(H) is the probability of the hypothesis occurring, independent of the reads D,
P(D|H) the probability of the reads D occurring given the hypothesis
$\Sigma P(H) \times P(D|H)$ is the sum of all probabilities for all hypotheses—which is used to normalise the results.

4. The method according to any one of the preceding embodiments wherein preliminary alignment is based on reads being positioned with respect to a reference genome to a required confidence level.

5. The method according to embodiment 4 wherein at least some reads that cannot initially be aligned are combined to form one or more assembly of reads that are utilised during preliminary alignment.

6. The method according to embodiment 5 wherein reads associated with aligned reads are included in an assembly of reads.

7. The method according to embodiment 6 wherein association includes matching paired end reads.

8. The method according to embodiment 6 wherein reads associated with external reference sequences are combined to form assemblies of reads.

9. The method according to any one of the preceding embodiments wherein a region is considered a complex calling region where the confidence in calling the region is below a first threshold.

10. The method according to any one of the preceding embodiments wherein a region is considered a region of interest where the confidence in calling the region is below a second threshold, higher than the first threshold, and where a region of interest occurs within a defined number of values of a complex calling region the complex calling region is expanded to encompass the region of interest and intermediate values up to and including the complex calling region.

11. The method according to any one of embodiments 1 to 10 wherein the hypotheses are the read values occurring in the complex calling region.

12. The method according to any one of embodiments 1 to 10 wherein the hypotheses are all possible sequence values in the complex calling region.

13. The method according to any one of the preceding embodiments wherein hypotheses are filtered to eliminate those with a probability below a prescribed threshold.

14. The method according to embodiment 13 wherein hypotheses having a frequency of occurrence below a threshold level are filtered out.

15. The method according to embodiment 13 wherein hypotheses having a low frequency of occurrence in similar populations from historic SNP data are filtered out.

16. The method according to any one of the preceding embodiments wherein the probability of a hypothesis occurring is based on historical genomic sequence data.

17. The method according to any one of the preceding embodiments wherein the probability of a hypothesis occurring takes into account phasing information.

18. The method according to any one of the preceding embodiments wherein the probability of each hypothesis representing a correct alignment is dependent at least in part upon a quality score for a sequencing machine of a type that provided the reads.

19. The method according to any one of the preceding embodiments wherein the probability of each hypothesis representing a correct alignment is dependent at least in part upon calibrated quality scores for the reads.

20. The method according to any one of the preceding embodiments wherein the probability of each hypothesis representing a correct alignment is dependent at least in part upon map scores assessing the quality of mapping of a hypothesis to a particular location of a reference sequence.

21. The method according to any one of the preceding embodiments wherein the probability of each hypothesis representing a correct alignment is dependent at least in part upon the chemistry of the sequences.

22. The method according to any one of the preceding embodiments wherein hypotheses are filtered.

23. The method according to embodiment 22 wherein hypotheses having a frequency of occurrence below a threshold level are filtered out.

24. The method according to embodiment 22 wherein hypotheses having a low frequency of occurrence in similar populations from historic SNP data are filtered out.

25. The method according to any one of the preceding embodiments wherein each hypothesis is evaluated with respect to each read considering at each sequence position the possibility of modification of a sequence value.

26. The method according to embodiment 25 wherein the modification is an indel.

27. The method according to embodiment 26 wherein the probability of an insertion is based on tables giving the probability of the insertion based on a previous or subsequent sequence position.

28. The method according to embodiment 26 wherein the probability of an insertion is based on tables giving the probability of the insertion based on multiple previous or subsequent sequence positions.

29. The method according to any one of embodiments 26 to 28 wherein the probability of a deletion is based on tables giving the probability of the deletion based on a previous or subsequent sequence position.

30. The method according to any one of embodiments 26 to 28 wherein the probability of a deletion is based on tables giving the probability of the deletion based on multiple previous or subsequent sequence positions.

31. The method according to any one of embodiments 25 to 30 wherein the probability for each hypothesis is the sum of all probabilities for all permutations of all reads.

32. The method according to embodiment 31 wherein calculated probabilities are cached and utilized to avoid recalculation.

33. The method according to any one of the preceding embodiments wherein the sequences are DNA sequences.

34. The method according to any one of embodiments 1 to 32 wherein the sequences are RNA sequences.

35. The method according to any one of embodiments 1 to 32 wherein the sequences are protein sequences.

36. The method according to any one of the preceding embodiments wherein the probability of one or more hypothesis is calculated in relation to a plurality of sequence types.

37. The method according to embodiment 36 wherein the two sequence types are DNA and protein sequences, or DNA and RNA sequences.

38. The method according to any one of the preceding embodiments wherein the complex calling region is a single sequence value.

39. The method according to any one of embodiments 1 to 38 wherein the complex calling region includes multiple sequence values.

40. The method as claimed in any one of the preceding claims, wherein the method comprises obtaining at least some of the read values by sequencing a sample prior to performing the preliminary sequence alignment.

41. A system for calling genomic sequence values in complex calling regions based on a plurality of read values, the system comprising:
one or more processors configured to execute one or more modules;
and a memory storing the one or more modules, the modules comprising:
a. code for performing a preliminary sequence alignment based on the reads;
b. code for identifying a complex calling region where no values satisfy preliminary alignment criteria;
c. code for formulating a plurality of hypotheses as to the sequence values in the complex calling region;
d. code for calculating the probability of each hypothesis representing a correct alignment by evaluating the probability of each hypothesis being correct for the reads and the probability of each hypothesis occurring; and
e. code for selecting the hypothesis best satisfying hypothesis selection criteria.

42. A method of calling genomic sequence values for a region based on a plurality of read values, the method performed by one or more processors executing program instructions stored on one or more memories, the instructions causing the one or more processors to perform the method comprising:
a. formulating a plurality of hypotheses as to the sequence values in the region;
b. calculating the probability of each hypothesis representing a correct alignment by evaluating the probability of each hypothesis occurring and the probability of each hypothesis being correct for the reads considering at each sequence position the possibility of modification of a sequence value; and
c. selecting the hypothesis best satisfying hypothesis selection criteria.

Other embodiments of the invention will be apparent to those skilled in the art from consideration of the specification and practice of the invention disclosed herein. Additional advantages and modifications will readily appear to those skilled in the art. Therefore, the invention in its broader aspects is not limited to the specific details, representative figures, and illustrative examples shown and described. Accordingly, departures may be made from such details without departure from the spirit or scope of the applicant's general inventive concept. It is intended that the specification and examples be considered as exemplary only, with a true scope and spirit of the invention being indicated by the following claims.

What is claimed is:

1. A method of calling genomic sequence values in complex calling regions based on a plurality of read values, the method performed by one or more processors executing program instructions stored on one or more memories, the instructions causing the one or more processors to perform the method comprising:
a. performing a preliminary sequence alignment based on the reads being positioned with respect to a reference genome at a required confidence level, wherein at least some reads that cannot initially be aligned are combined to form one or more assembly of reads that are utilised during the preliminary alignment;
b. identifying a complex calling region where no values satisfy preliminary alignment criteria;
c. formulating a plurality of hypotheses as to the sequence values in the complex calling region;
d. calculating the probability of each hypothesis representing a correct alignment by evaluating the probability of each hypothesis being correct for the reads and the probability of each hypothesis occurring; and
e. selecting the hypothesis best satisfying hypothesis selection criteria.

2. The method as claimed in claim 1 wherein the probability of a hypothesis being correct for the reads is calculated according to:

$$P(H|D) = \frac{P(H) \times P(D|H)}{\sum P(H) \times P(D|H)}$$

where:
P(H|D) is the probability of a hypothesis H being correct for all reads D,
P(H) is the probability of the hypothesis occurring, independent of the reads D,
P(D|H) the probability of the reads D occurring given the hypothesis
Σ(H)×P(D|H) is the sum of all probabilities for all hypotheses—which is used to normalise the results.

3. The method as claimed in claim 1 wherein reads associated with aligned reads are included in an assembly of reads.

4. The method as claimed in claim 3 wherein the reads associated with aligned reads include matching paired end reads.

5. The method according to claim 3 wherein the reads associated with external reference sequences are combined to form assemblies of reads.

6. A method of calling genomic sequence values in complex calling regions based on a plurality of read values, the method performed by one or more processors executing program instructions stored on one or more memories, the instructions causing the one or more processors to perform the method comprising:
   a. performing a preliminary sequence alignment based on the reads;
   b. identifying a complex calling region where no values satisfy preliminary alignment criteria, wherein a region is considered a complex calling region where the confidence in calling the region is below a first threshold, a region is considered a region of interest where the confidence in calling the region is below a second threshold, the second threshold being higher than the first threshold, and where a region of interest occurs within a defined number of values of a complex calling region the complex calling region is expanded to encompass the region of interest and intermediate values up to and including the complex calling region;
   c. formulating a plurality of hypotheses as to the sequence values in the complex calling region;
   d. calculating the probability of each hypothesis representing a correct alignment by evaluating the probability of each hypothesis being correct for the reads and the probability of each hypothesis occurring; and
   e. selecting the hypothesis best satisfying hypothesis selection criteria.

7. The method as claimed claim 1 wherein the hypotheses are the read values occurring in the complex calling region or all possible sequence values in the complex calling region.

8. The method as claimed in claim 1 wherein hypotheses are filtered to eliminate those with a probability below a prescribed threshold.

9. The method as claimed claim 1 wherein hypotheses having a low frequency of occurrence in similar populations from historic SNP data are filtered out.

10. The method as claimed in claim 1 wherein the probability of a hypothesis occurring is based on historical genomic sequence data.

11. The method as claimed in claim 1 wherein the probability of a hypothesis occurring takes into account phasing information.

12. The method as claimed in claim 1 wherein the probability of each hypothesis representing a correct alignment is dependent at least in part upon one or more of a quality score for a sequencing machine of a type that provided the reads, calibrated quality scores for the reads, map scores assessing the quality of mapping of a hypothesis to a particular location of a reference sequence, and the chemistry of the sequences.

13. A method of calling genomic sequence values in complex calling regions based on a plurality of read values, the method performed by one or more processors executing program instructions stored on one or more memories, the instructions causing the one or more processors to perform the method comprising:
   a. performing a preliminary sequence alignment based on the reads;
   b. identifying a complex calling region where no values satisfy preliminary alignment criteria;
   c. formulating a plurality of hypotheses as to the sequence values in the complex calling region;
   d. calculating the probability of each hypothesis representing a correct alignment by evaluating the probability of each hypothesis being correct for the reads and the probability of each hypothesis occurring; and
   e. selecting the hypothesis best satisfying hypothesis selection criteria,
   wherein each hypothesis is evaluated with respect to each read considering at each sequence position the possibility of an indel.

14. The method as claimed in claim 13 wherein the probability of an insertion is based on tables giving the probability of the insertion based on a previous sequence position or on multiple previous sequence positions.

15. The method as claimed in claim 13 wherein the probability for each hypothesis is the sum of all probabilities for all permutations of all reads.

16. The method as claimed in claim 1 wherein the sequences are DNA or RNA sequences.

17. The method as claimed in claim 1 wherein the sequences are protein sequences.

18. The method as claimed in claim 1 wherein the probability of one or more hypotheses is calculated in relation to (i) DNA or RNA sequences and (ii) protein sequences.

19. The method as claimed in claim 1 wherein the complex calling region is a single sequence value.

20. The method as claimed in claim 1 wherein the complex calling region includes multiple sequence values.

21. The method as claimed in claim 1, wherein the method comprises obtaining at least some of the read values by sequencing a sample prior to performing the preliminary sequence alignment.

22. A system for calling genomic sequence values in complex calling regions based on a plurality of read values, the system comprising:
   one or more processors configured to execute one or more modules;
   and a memory storing the one or more modules, the modules comprising:
   a. code for performing a preliminary sequence alignment based on the reads being positioned with respect to a reference genome at a required confidence level, wherein at least some reads that cannot initially be aligned are combined to form one or more assembly of reads that are utilised during the preliminary alignment;
   b. code for identifying a complex calling region where no values satisfy preliminary alignment criteria;
   c. code for formulating a plurality of hypotheses as to the sequence values in the complex calling region;
   d. code for calculating the probability of each hypothesis representing a correct alignment by evaluating the probability of each hypothesis being correct for the reads and the probability of each hypothesis occurring; and e. code for selecting the hypothesis best satisfying hypothesis selection criteria.

23. A method of calling genomic sequence values for a region based on a plurality of read values, the method performed by one or more processors executing program instructions stored on one or more memories, the instructions causing the one or more processors to perform the method comprising:
   a. formulating a plurality of hypotheses as to the sequence values in the region;
   b. calculating the probability of each hypothesis representing a correct alignment by evaluating the probability of each hypothesis occurring and the probability of each hypothesis being correct for the reads considering at each sequence position the possibility of modification of a sequence value; and
   c. selecting the hypothesis best satisfying hypothesis selection criteria,
   wherein each hypothesis is evaluated with respect to each read considering at each sequence position the possibility of an indel.

\* \* \* \* \*